United States Patent
Takei et al.

(10) Patent No.: US 9,750,562 B2
(45) Date of Patent: Sep. 5, 2017

(54) TREATMENT INSTRUMENT

(71) Applicant: OLYMPUS CORPORATION, Hachioji-shi, Tokyo (JP)

(72) Inventors: Yusuke Takei, Hino (JP); Tomoyuki Takashino, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/235,664

(22) Filed: Aug. 12, 2016

(65) Prior Publication Data
US 2016/0346035 A1 Dec. 1, 2016

Related U.S. Application Data

(63) Continuation of application No. PCT/JP2015/053266, filed on Feb. 5, 2015.

(30) Foreign Application Priority Data

Feb. 12, 2014 (JP) ................................. 2014-024753

(51) Int. Cl.
*A61B 18/14* (2006.01)
*A61B 18/08* (2006.01)
*A61B 18/00* (2006.01)

(52) U.S. Cl.
CPC ........ *A61B 18/1445* (2013.01); *A61B 18/085* (2013.01); *A61B 18/1482* (2013.01);
(Continued)

(58) Field of Classification Search
CPC ............ A61B 18/1445; A61B 18/1442; A61B 18/085; A61B 2018/1452;
(Continued)

(56) References Cited

U.S. PATENT DOCUMENTS 6,113,598 A * 9/2000 Baker ................ A61B 18/1445
606/38
6,126,658 A * 10/2000 Baker ................ A61B 18/1445
606/38
(Continued)

FOREIGN PATENT DOCUMENTS

JP 2008-508966 A 3/2008

OTHER PUBLICATIONS

Mar. 24, 2015 International Search Report issued in Patent Application No. PCT/JP2015/053266.
(Continued)

*Primary Examiner* — Thomas Giuliani
(74) *Attorney, Agent, or Firm* — Oliff PLC

(57) ABSTRACT

A treatment instrument includes a first clamping surface, a second clamping surface configured to cooperate with the first clamping surface and to clamp a living body tissue, a pressure application member provided on one of the first and second clamping surfaces, and configured to apply a pressure to the living body tissue in a line shape by causing the first and second clamping surfaces to relatively approach each other, and a moving mechanism provided on the first clamping surface, and configured to move the first clamping surface in a manner to apply tensile forces to the living body tissue, clamped between the first and second clamping surfaces, in directions deviating away from a direction along a line formed on the living body tissue by the pressure application member.

13 Claims, 11 Drawing Sheets

(52) U.S. Cl.
CPC ............... *A61B 2018/0063* (2013.01); *A61B 2018/00595* (2013.01); *A61B 2018/00601* (2013.01); *A61B 2018/00696* (2013.01); *A61B 2018/1462* (2013.01)

(58) Field of Classification Search
CPC .. A61B 2018/1455; A61B 2018/00607; A61B 2018/00595; A61B 2018/00601; A61B 2018/0063
USPC ..................................... 606/50–52, 205, 207
See application file for complete search history.

(56) References Cited

U.S. PATENT DOCUMENTS

| | | | |
|---|---|---|---|
| 6,132,429 A * | 10/2000 | Baker ............... | A61B 18/1442 606/38 |
| 7,534,243 B1 | 5/2009 | Chin et al. | |
| 2003/0212420 A1 | 11/2003 | Gruhl et al. | |

OTHER PUBLICATIONS

Mar. 1, 2016 Office Action issued in Japanese Patent Application No. 2015-545578.
Translation of Aug. 16, 2016 International Preliminary Report on Patentability issued in International Patent Application No. PCT/JP2015/053266.

* cited by examiner

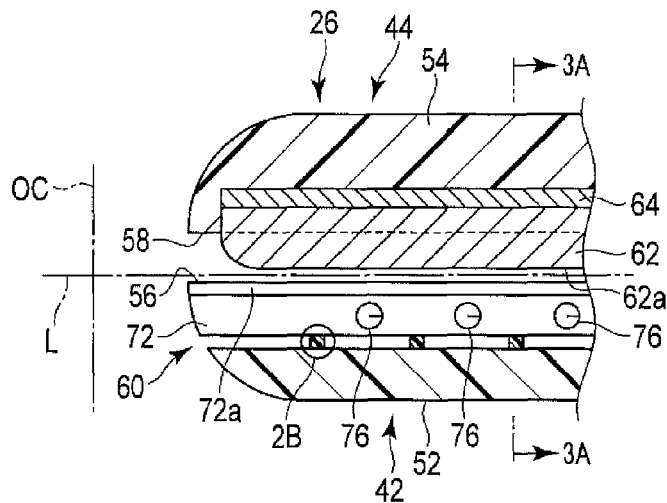
F I G. 2A
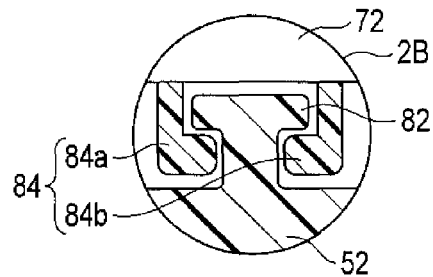
F I G. 2B
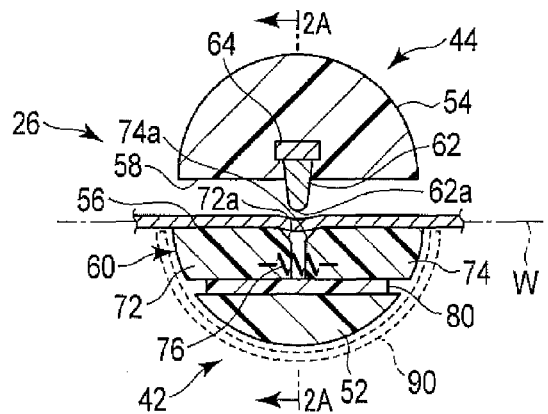
F I G. 3A

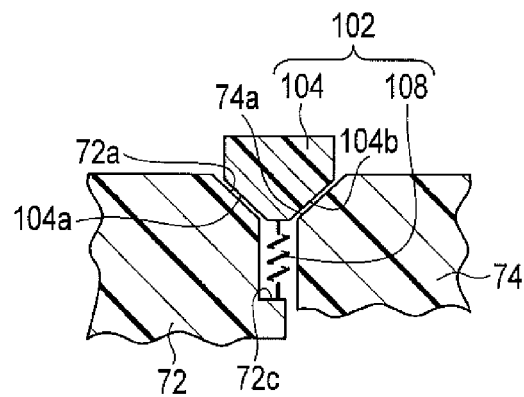
F I G. 6C
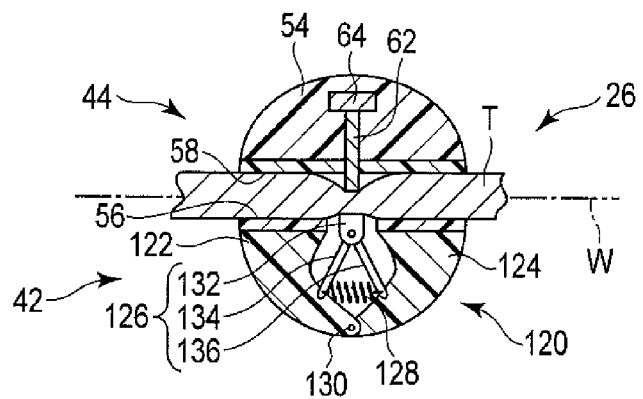
F I G. 7A
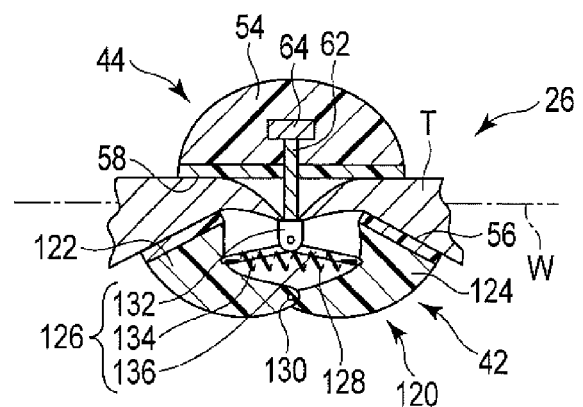
F I G. 7B

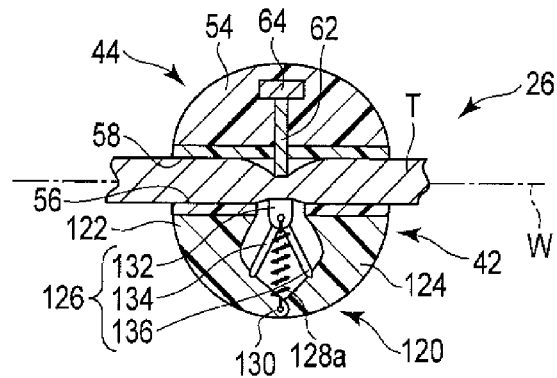
F I G. 8A
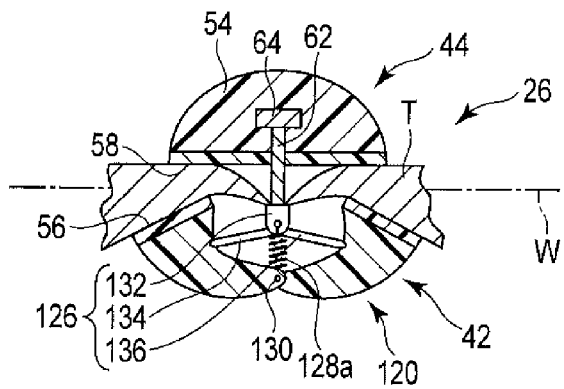
F I G. 8B
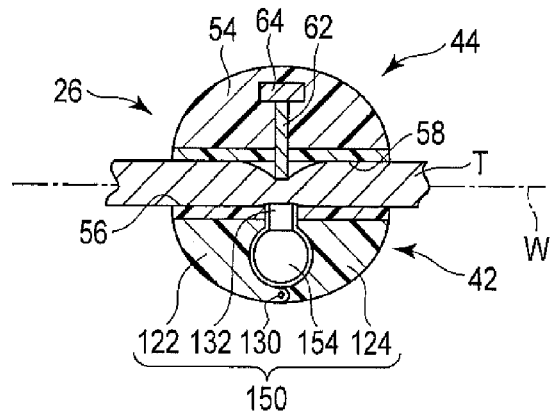
F I G. 9A

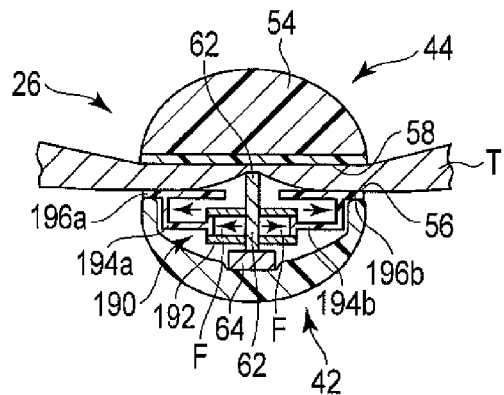
F I G. 12B
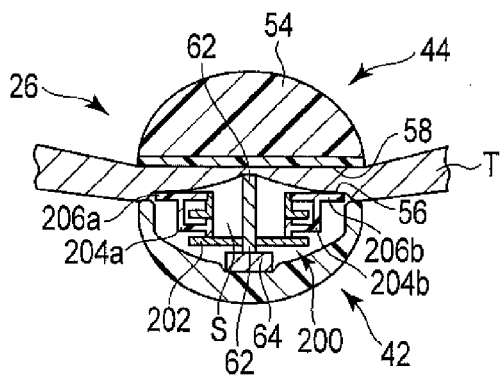
F I G. 13A
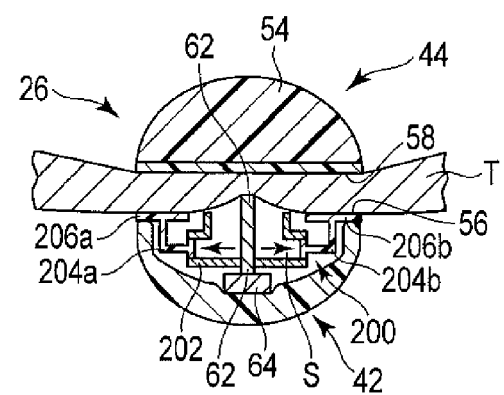
F I G. 13B

TREATMENT INSTRUMENT

CROSS-REFERENCE TO RELATED APPLICATIONS

This application is a Continuation application of PCT Application No. PCT/JP2015/053266, filed Feb. 5, 2015 and based upon and claiming the benefit of priority from prior Japanese Patent Application No. 2014-024753, filed Feb. 12, 2014, the entire contents of all of which are incorporated herein by reference.

BACKGROUND OF THE INVENTION

1. Field of the Invention

The present invention relates to a treatment instrument which treats a living body tissue.

2. Description of the Related Art

For example, U.S. Patent Application Publication No. 2003/0212420 discloses a treatment instrument including an end effector which clamps a living body tissue by two pairs of jaws (clamping portions), and locally heats the living body tissue by cautery pads disposed on grasping surfaces of the jaws, thus being capable of sealing the living body tissue. This treatment instrument heats the living body tissue in the state in which the two pairs of jaws are positioned close to each other, and treats the living body tissue between the two pairs of jaws. In this treatment instrument, after the living body tissue between the two pairs of jaws was treated, the two pair of jaws are moved forward, relative to the shaft. Thereby, one pair of jaws are moved away from the other pair of jaws, and force can be applied so as to separate the cauterized living body tissue between the two pairs of jaws.

BRIEF SUMMARY OF THE INVENTION

According to one aspect of the present invention, a treatment instrument includes: a first clamping surface; a second clamping surface which is opposed to the first clamping surface such that the second clamping surface is capable of relatively approaching, and moving away from, the first clamping surface, and which is configured to cooperate with the first clamping surface and to clamp a living body tissue by causing the first clamping surface to relatively approach the second clamping surface; a pressure application member which is provided on one of the first and second clamping surfaces, and which is configured to apply a pressure to the living body tissue in a line shape by causing the first and second clamping surfaces to relatively approach each other; and a moving mechanism which is provided on the first clamping surface, and which is configured to move the first clamping surface in a manner to apply tensile forces to the living body tissue, which is clamped between the first and second clamping surfaces, in directions deviating away from a direction along a line formed on the living body tissue by the pressure application member.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2A is a schematic longitudinal cross-sectional view illustrating an end effector of a treatment instrument of the treatment system according to the first embodiment.

FIG. 2B is a schematic view illustrating, in enlarged scale, a part designated by numeral 2B in FIG. 2A.

FIG. 3A is a schematic transverse cross-sectional view illustrating the end effector of the treatment instrument of the treatment system according to the first embodiment, and illustrating a state in which first and second clamping surfaces are spaced apart, and an abutment portion of a pushing body is separated from a living body tissue.

FIG. 6C is a schematic transverse cross-sectional view illustrating a support state of a support portion which is disposed on the oblique surfaces of the first and second separate bodies of the end effector of the treatment instrument of the treatment system according to the second modification of the first embodiment.

FIG. 7A is a schematic transverse cross-sectional view illustrating an end effector of a treatment instrument of a treatment system according to a third modification of the first embodiment, and illustrating a state in which a living body tissue is clamped between first and second clamping surfaces, while a pushing force is being applied to the living body tissue by an abutment portion of a pushing body.

FIG. 7B is a schematic transverse cross-sectional view illustrating the end effector of the treatment instrument of the treatment system according to the third modification of the first embodiment, and illustrating a state in which the first and second clamping surfaces are moved to approach each other, a pushing force is applied to the living body tissue by the abutment portion of the pushing body, and first and second separate bodies are moved in directions away from each other.

FIG. 8A is a schematic transverse cross-sectional view illustrating an end effector of a treatment instrument of a treatment system according to a fourth modification of the first embodiment, and illustrating a state in which a living body tissue is clamped between first and second clamping surfaces, while a pushing force is being applied to the living body tissue by an abutment portion of a pushing body.

FIG. 8B is a schematic transverse cross-sectional view illustrating the end effector of the treatment instrument of the treatment system according to the fourth modification of the first embodiment, and illustrating a state in which the first and second clamping surfaces are moved to approach each other, a pushing force is applied to the living body tissue by the abutment portion of the pushing body, and first and second separate bodies are moved in directions away from each other.

FIG. 9A is a schematic transverse cross-sectional view illustrating an end effector of a treatment instrument of a treatment system according to a fifth modification of the first embodiment, and illustrating a state in which a living body tissue is clamped between first and second clamping surfaces, while a pushing force is being applied to the living body tissue by an abutment portion of a pushing body.

FIG. 12B is a schematic transverse cross-sectional view illustrating the end effector of the treatment instrument of the treatment system according to the second modification of the second embodiment, and illustrating a state in which a liquid in a cylinder is heated and vaporized by a heater and first and second separate bodies are moved in directions away from each other by pistons disposed in the cylinder, in the state in which the living body tissue is clamped between the first and second clamping surfaces while the pushing force is being applied to the living body tissue by the abutment portion of the pushing body.

FIG. 13A is a schematic transverse cross-sectional view illustrating an end effector of a treatment instrument of a treatment system according to a third modification of the second embodiment, and illustrating a state in which a living body tissue is clamped between first and second clamping surfaces, while a pushing force is being applied to the living body tissue by an abutment portion of a pushing body.

FIG. 13B is a schematic transverse cross-sectional view illustrating the end effector of the treatment instrument of the treatment system according to the third modification of the second embodiment, and illustrating a state in which a pushing body disposed in a cylinder is heated by a heater in the state in which the living body tissue is clamped between the first and second clamping surfaces while the pushing force is being applied to the living body tissue by the abutment portion of the pushing body, and first and second separate bodies are moved in directions away from each other by pistons disposed in the cylinder by using steam released from the living body tissue by the heat of the heater.

DETAILED DESCRIPTION OF THE INVENTION

Hereinafter, embodiments for implementing the present invention will be described with reference to the accompanying drawings.

A first embodiment is described with reference to FIG. 1 to FIG. 3B.

Figure 1:
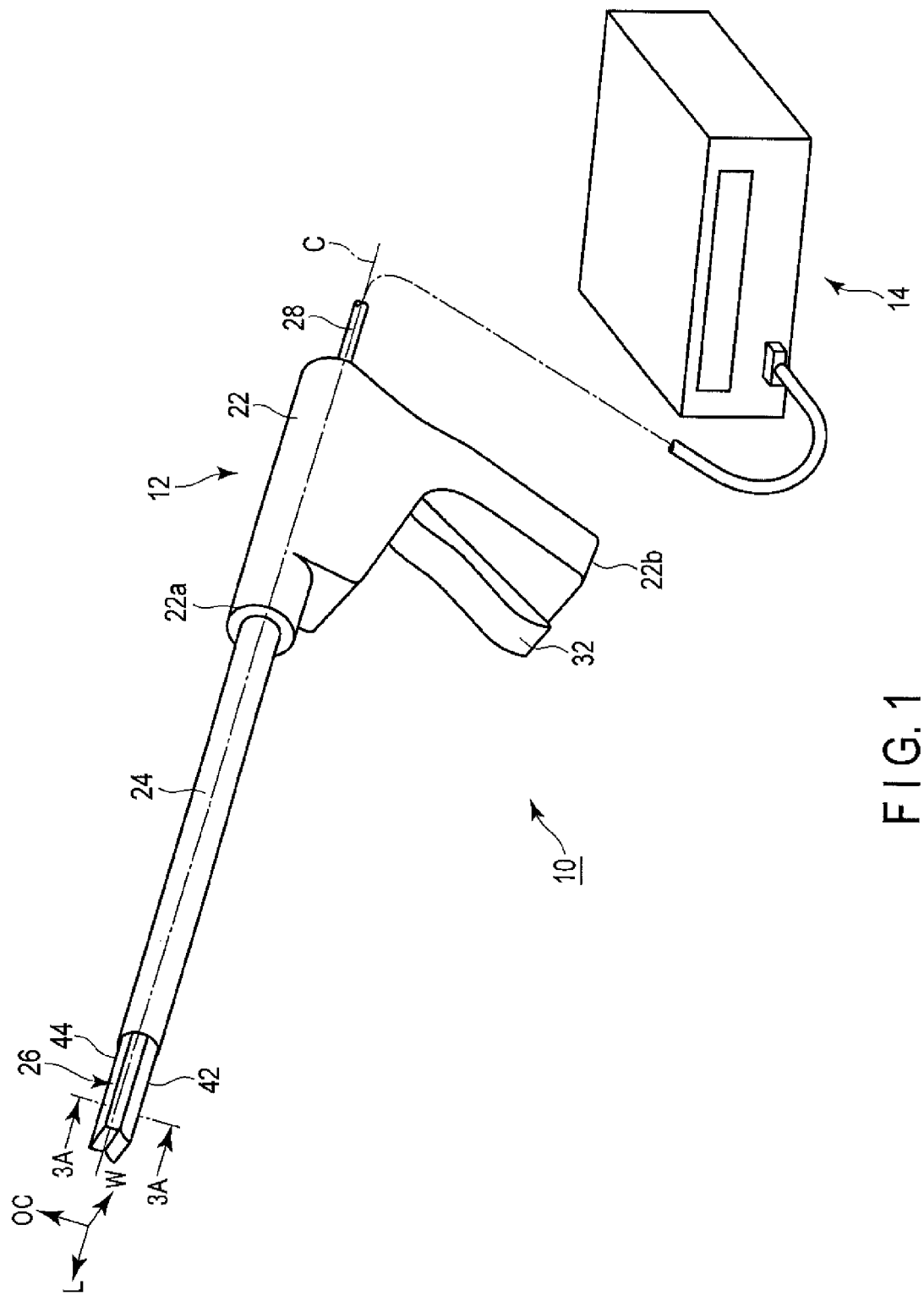
FIG. 1 is a schematic perspective view illustrating a treatment system according to first to third embodiments including modifications.

As illustrated in FIG. 1, a therapeutic treatment system 10 includes a treatment instrument (therapeutic treatment device) 12, and an energy source (controller) 14.

The treatment instrument 12 includes a handle 22, a shaft 24 having a center axis C, and an end effector 26. The energy source 14 is connected to the handle 22 via a cable 28. It is preferable that a footswitch (not shown) is connected to the energy source 14. A surgeon (user) operates a pedal of the footswitch by the foot, thereby switching the ON/OFF of energy supply from the energy source 14 to the end effector 26 of the treatment instrument 12. In this embodiment, if the pedal is pushed, a heater 64 (to be described later) is heated, and the heat of the heater 64 is conveyed to a pushing body 62.

The handle 22 is formed in a substantially L-shape. The shaft 24 is provided at one end (distal end) 22a of the handle 22. For example, the above-described cable 28 extends from a proximal end of the handle 22, which is substantially coaxial with the shaft 24.

The other end 22b of the handle 22 is a grasping portion which is grasped by the surgeon. The handle 22 includes an opening/closing knob (operation element) 32, such that the opening/closing knob 32 is juxtaposed with the other end 22b. In this embodiment, the opening/closing knob 32 is disposed on the front side of the other end 22b of the handle 22. The opening/closing knob 32 is made rotatable by a pivotal support shaft (not shown) within the handle 22. Thus, the opening/closing knob 32 can be moved toward and away from the other end of the handle 22.

The opening/closing knob 32 is formed as a part of a publicly known opening/closing mechanism which can relatively open/close first and second clamping bodies 52 and 54 (to be described later) of the end effector 26. If the opening/closing knob 32 is operated relative to the other end 22b of the handle 22, first and second clamping surfaces 56 and 58 can be moved toward and away from each other in an opening/closing direction OC. For example, if the opening/closing knob 32 is moved toward the other end 22b of the handle 22 by the publicly known opening/closing mechanism, the first and second clamping bodies 52 and 54 can be relatively moved to approach each other, or in other words, can be closed. If the opening/closing knob 32 is moved away from the other end 22b of the handle 22, the first and second clamping bodies 52 and 54 can be relatively moved away from each other, or in other words, can be opened.

As illustrated in FIG. 1, in this embodiment, the end effector 26 is disposed at a distal end of the shaft 24.

As illustrated in FIG. 2A, FIG. 3A, FIG. 3B and FIG. 4A, the end effector 26 includes a first clamping portion 42 and a second clamping portion 44. The end effector 26 includes first and second clamping bodies 52 and 54 which are relatively movable in the opening/closing direction OC in accordance with the operation of the opening/closing knob 32, that is, movable toward and away from each other; a first clamping surface 56 provided on the first clamping body 52; a second clamping surface 58 provided on the second clamping body 54; a moving mechanism 60 provided on the first clamping body 52; and a pushing body (pressure application member) 62 provided on the second clamping surface 58. The second clamping surface 58 is opposed to the first clamping surface 56, and clamps a living body tissue in cooperation with the first clamping surface 56. It is preferable that each of the first and second clamping surfaces 56 and 58 is formed in a substantially rectangular shape. Thus, a longitudinal direction L and a width direction W are defined for each of the first and second clamping surfaces 56 and 58.

Specifically, in this embodiment, the first clamping portion 42 includes the first clamping body 52, first clamping surface 56, and moving mechanism 60 provided on the first clamping surface 56. The second clamping portion 44 includes the second clamping body 54, second clamping surface 58, and pushing body 62 projecting from the second clamping surface 58 toward the first clamping surface 56.

Outer surfaces of the first and second clamping bodies 52 and 54, which are located on the sides opposite to the first and second clamping surfaces 56 and 58, are formed in smooth curved shapes. It is preferable that the first and second clamping bodies 52 and 54 have electrical insulation properties in order to prevent an electric current from flowing, when not intended, to a living body tissue from some other device through the first and second clamping bodies 52 and 54.

The moving mechanism 60 can move the first clamping surface 56 so as to apply tensile forces to the living body tissue, which is clamped between the first and second clamping surfaces 56 and 58, in directions away from a direction along a line formed on the living body tissue by the pushing body 62, and can apply such a force as to split the living body tissue along this line. Specifically, the moving mechanism 60 according to this embodiment can move the first clamping surface 56 so as to apply tensile forces to the living body tissue, which is clamped between the first and second clamping surfaces 56 and 58, in directions perpendicular to the direction in which the first and second clamping surfaces 56 and 58 can be relatively moved toward and away from each other. In this embodiment, the first clamping surface 56 is separated into two parts at a substantially middle point in the width direction W which is perpendicular to the longitudinal direction L.

In this embodiment, the pushing body 62 is formed in a plate shape. The pushing body 62 is located at a substantially middle point in the width direction W. The pushing body 62 is supported by the second clamping body 54 in a manner to penetrate the second clamping surface 58, and projects toward the first clamping surface 56. Thus, the pushing body 62 can apply a pressure to the living body tissue, and can split the living body tissue in the direction (width direction) in which the above-described tensile forces are applied. It is preferable that the transverse cross-sectional area of the pushing body 62 is formed thicker at a position of the second clamping surface 58 than at a position close to the first clamping surface 56 (a position away from the second clamping surface 58). The pushing body 62 includes, at a position close to the first clamping surface 56, an abutment portion (pressure application portion) 62a which can apply thermal energy to the living body tissue. The abutment portion 62a is a portion which abuts on the living body tissue and applies a pressure in a line shape by relatively moving the first and second clamping surfaces 56 and 58 into close proximity to each other, and the abutment portion 62a should preferably have a blunt shape. In other words, the abutment portion 62a does not need to be formed in a sharp shape. The pushing body 62 can apply a pressure to the living body tissue in a line shape by the abutment portion 62a, and can split the living body tissue in the direction in which the above-described tensile forces are applied (width direction W in this example).

Figure 4A:
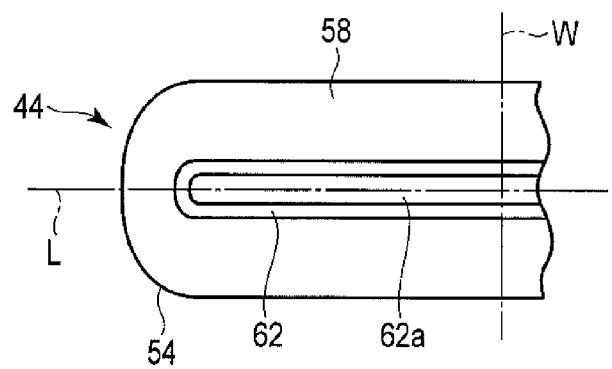
FIG. 4A is a schematic view illustrating the second clamping surface and pushing body of the end effector of the treatment instrument of the treatment system according to the first embodiment.
Figure 4B:
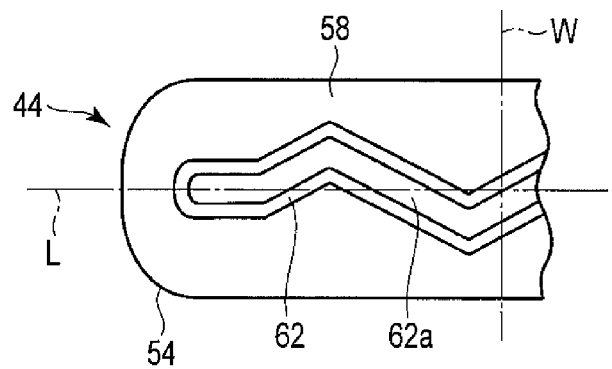
FIG. 4B is a schematic view illustrating the second clamping surface of the end effector of the treatment instrument of the treatment system according to the first embodiment, and a pushing body having a shape that is changed, compared to FIG. 4A.

The pushing body 62 may be straight along the longitudinal direction L, as illustrated in FIG. 4A, or may preferably have a meandering shape deviating from the longitudinal direction L, as illustrated in FIG. 4B. In the meantime, the shape of the first clamping surface 56 is formed in a manner to correspond to the shape of the abutment portion 62a of the pushing body 62, and, specifically, oblique surfaces 72a and 74a of first and second separate bodies 72 and 74 (to be described later) are formed. In other words, the first and second separate bodies 72 and 74 are formed such that the abutment portion 62a of the pushing body 62 linearly abuts on, and applies a pressure in a line shape to, the oblique surfaces 72a and 74a of the first and second separate bodies 72 and 74, when the first and second clamping surfaces 56 and 58 are moved in close proximity.

Figure 3B:
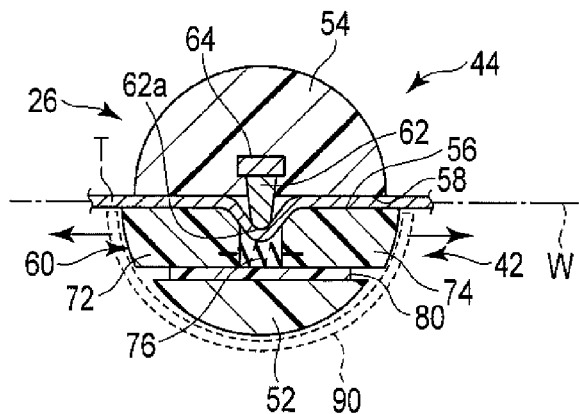
FIG. 3B is a schematic transverse cross-sectional view illustrating the end effector of the treatment instrument of the treatment system according to the first embodiment, and illustrating a state in which the first and second clamping surfaces are moved to approach each other, a pushing force is applied to the living body tissue by the abutment portion of the pushing body provided on the second clamping surface, and first and second separate bodies provided on the first clamping surface are moved in directions away from each other.

As illustrated in FIG. 2A, FIG. 3A and FIG. 3B, the heater 64, which conveys heat to the pushing body 62, is disposed between the second clamping body 54 and pushing body 62. It is preferable that the heater 64 has a thin plate shape with a thickness of less than several millimeters. It is preferable that the abutment portion 62a of the pushing body 62 can be heated up to, for example, about 200° C. to 350° C., by the heater 64.

In addition, the pushing body 62 is formed of a material which can easily convey heat from the heater 64 to the living body tissue. It is preferable that the pushing body 62 is formed of a metallic material with good heat conductivity, such as copper or aluminum.

It is preferable that the second clamping body 54, in which the heater 64 is disposed, has heat resistance and adiathermancy. Thus, even if the heater 64 is caused to produce heat, it is possible to prevent the second clamping body 54 from being damaged, and to prevent the heat from the heater 64 from being conveyed, when not intended, to the living body tissue existing in the vicinity of the second clamping body 54.

Incidentally, it is preferable that the first clamping body 52, too, is formed of a material with heat resistance and adiathermancy.

The moving mechanism 60, which is provided on the first clamping body 52, includes a first separate body 72, a second separate body 74, and an urging member 76 which urges the first and second separate bodies 72 and 74 to approach, or abut on, each other. In this embodiment, it is preferable that the first and second separate bodies 72 and 74 have symmetric shapes with respect to an imaginary plane of the pushing body 62, which is imaginarily defined by the pushing body 62 moving in accordance with the opening/closing of the first and second clamping bodies 52 and 54. The first and second separate bodies 72 and 74 form the first clamping surface 56.

It is preferable that the first and second separate bodies 72 and 74 have heat resistance and adiathermancy, like the first and second clamping bodies 52 and 54.

Each of the first and second separate bodies 72 and 74 has a substantially fan-shaped transverse cross section. Oblique surfaces 72a and 74a, which serve as support portions for supporting the pushing body 62, are formed on those edge portions of the first and second separate bodies 72 and 74, which are located on the first clamping surface 56 side. When the abutment portion 62a of the pushing body 62 abuts upon and pushes the oblique surfaces 72a and 74a, the oblique surfaces 72a and 74a support the pushing body 62 so as to move the first and second separate bodies 72 and 74 away from each other. In the meantime, when the abutment portion 62a of the pushing body 62 does not abut upon the oblique surfaces 72a and 74a, the first and second separate bodies 72 and 74 may be in contact with each other, or a gap may be formed therebetween.

A slide mechanism 80 is disposed between the first clamping body 52 and the first and second separate bodies 72 and 74. The slide mechanism 80 according to this embodiment can move the first and second separate bodies 72 and 74 only in the width direction W. In addition, the slide mechanism 80 prevents a displacement of the first and second separate bodies 72 and 74 in the opening/closing direction OC.

As illustrated in FIG. 2B, the slide mechanism 80 includes a clamping body-side slide portion 82 and a separate body-side slide portion 84. Here, the clamping body-side slide portion 82 is formed in a substantially T shape, and is elongated along the width direction W. The separate body-side slide portion 84 includes a pair of L-shaped members 84a and 84b which are elongated along the width direction W in a manner to sandwich the clamping body-side slide portion 82. Incidentally, it is preferable that not a single slide mechanism 80 but a plurality of slide mechanisms 80 are disposed.

In addition, the first and second separate bodies 72 and 74 are coupled by an urging member 76. It is preferable that a spring element, such as a tension coil spring, which urges the first and second separate bodies 72 and 74 to approach each other, is used as the urging member 76.

It is preferable that an elastically deformable cover 90, for example, is disposed on the outside of the first second separate bodies 72 and 74. It is thus possible to prevent a living body tissue or the like, which exists in the vicinity of the treatment-target living body tissue, from being clamped between the first and second separate bodies 72 and 74, or between the first clamping body 52 and moving mechanism 60. In addition, when the first clamping body 52 and the first and second separate bodies 72 and 74 of the moving mechanism, which were heated up to high temperatures after therapeutic treatment, have come in contact with a neighboring tissue, it is possible to prevent this neighboring tissue from being thermally affected.

Next, the operation of the treatment system 10 according to this embodiment is described. Here, as illustrated FIG. 4A, the description is given on the assumption that the pushing body 62 including the abutment portion 62a, which is straight in the longitudinal direction L, is used.

The opening/closing knob 32 is operated to open the first and second clamping surfaces 56 and 58 relative to each other, as illustrated in FIG. 3A, and a living body tissue T is placed on the first clamping surface 56. In this state, the opening/closing knob 32 is operated to close the first and second clamping surfaces 56 and 58 relative to each other. At this time, a pressure is applied to the living body tissue T in a line shape.

The living body tissue T is pushed toward the oblique surfaces 72a and 74a of the first and second separate bodies 72 and 74 by the abutment portion 62a of the pushing body 62. At this time, by the slide mechanism 80, the first and second separate bodies 72 and 74 move, against the urging force of the urging member 76, in a direction (here, the width direction W) which is perpendicular to the direction of movement of the pushing body 62 (the opening/closing direction OC in which the first and second clamping surfaces 56 and 58 move toward and away from each other). Specifically, the moving mechanism 60 moves the living body tissue T, which is clamped between the first and second clamping surfaces 56 and 58, in a direction (here, the width direction W) which is perpendicular to the direction (the opening/closing direction OC) in which the first and second clamping bodies 52 and 54 can be relatively moved toward and away from each other. Thus, tensile forces are applied to the living body tissue T in directions perpendicular to the direction in which the living body tissue T is pushed by the pushing body 62. In other words, forces, which try to split the clamped living body tissue T, are applied toward mutually opposite sides, with the abutment portion 62a of the pushing body 62 being interposed.

Here, for example, when the clamped living body tissue T has become fragile or thin, the living body tissue T can be split by applying, by the moving mechanism 60, forces (tensile forces) for splitting the living body tissue in mutually opposite directions away from the line formed on the living body tissue T by the pushing body 62, without supplying energy to the heater 64 from the energy source 14, or after finishing the application of the energy. Needless to say, it is also preferable that the living body tissue T is split while heating the living body tissue T by the abutment portion 62a of the pushing body 62 by supplying energy to the heater 64 from the energy source 14.

Besides, for example, when the living body tissue T is relatively thick, the pushing body 62 is heated by supplying energy to the heater 64 from the energy source 14. At this time, the abutment portion 62a of the pushing body 62 is heated up to, for example, about 200° C. to 350° C. In addition, tensile forces toward mutually opposite sides are applied to that part of the living body tissue T, which is put in contact with the abutment portion 62a of the pushing body 62, while hemostasis of this part is being effected by heat. In this manner, since the tensile forces toward mutually opposite sides are applied to the symmetric positions with the pushing body 62 being interposed, the living body tissue T can be split.

In the meantime, as illustrated in FIG. 4B, when the pushing body 62 including the meandering abutment portion 62a is used and oblique surfaces 72a and 74, which are formed in accordance with the shape of the meandering abutment portion 62a, are used, a pressure is applied to the living body tissue T in a meandering line shape. Tensile forces in directions deviating away from the line formed by the pushing of the pushing body 62 are applied to the living body tissue T to which the pressure was applied in the meandering line shape. In other words, forces, which try to split the living body tissue T, are applied toward mutually opposite sides, with the abutment portion 62a of the pushing body 62 being interposed. Thus, even in the case of using the pushing body 62 illustrated in FIG. 4B and the first and second separate bodies 72 and 74, the living body tissue T can be split like the case of using the pushing body 62 illustrated in FIG. 4A and the first and second separate bodies 72 and 74.

As has been described above, according to the treatment system 10 of the present embodiment, the following can be said.

The first and second separate bodies 72 and 74 of the moving mechanism 60 can apply such forces as to be able to move and separate the first clamping surface 56 in directions deviating from the direction of movement (opening/closing direction OC) of the pushing body 62 and in mutually opposite directions. The living body tissue, which is pushed by the abutment portion 62a of the plate-shaped pushing body 62, is pushed on the oblique surfaces 72a and 74a of the first and second separate bodies 72 and 74. Thereby, the first and second separate bodies 72 and 74 can be moved toward mutually opposite sides, with the abutment portion 62a being interposed. Thus, the tensile forces toward the opposite sides, with the pushing body 62 being interposed, can be applied to the living body tissue which is pushed by the abutment portion 62a of the pushing body 62. Accordingly, even if the abutment portion 62a is not sharp, the force can be applied to the living body tissue so that the living body tissue T can easily be split.

In this manner, according to the treatment instrument 12 of this embodiment, in the state in which the living body tissue is clamped, the clamped living body tissue can easily be split. In addition, the moving mechanism 60 is included in the first clamping portion 42 and simply moves within the first clamping portion 42. Thus, when the living body tissue of the treatment target (split target) is to be treated (split), the treatment can be performed while maintaining the positions of the end effector 26, shaft 24 and handle 22.

For example, even in the case of the living body tissue with a relatively great thickness, the living body tissue can easily be split even if the abutment portion 62a is not sharp, by applying heat to the living body tissue from the abutment portion 62a of the pushing body 62.

Therefore, according to the treatment system 10 of this embodiment, in the state in which the living body tissue is clamped, the clamped living body tissue can easily be split.

A first modification of the first embodiment will be described with reference to FIG. 5. Incidentally, in the subsequent embodiments including modifications following this modification, descriptions will be given of the treatment instrument 12 using the pushing body 62 having the shape illustrated in FIG. 4A.

Figure 5:
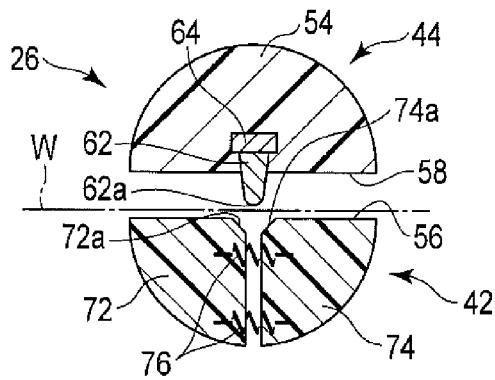
FIG. 5 is a schematic transverse cross-sectional view illustrating an end effector of a treatment instrument of a treatment system according to a first modification of the first embodiment, and illustrating a state in which first and second clamping surfaces are spaced apart, and an abutment portion of a pushing body is separated from a living body tissue.

As illustrated in FIG. 5, an end effector 26 according to this modification includes first and second clamping surfaces 56 and 58 which are relatively movable toward and away from each other; a moving mechanism 60 provided on the first clamping surface 56; and a pushing body (pressure application member) 62 provided on the second clamping surface 58. The second clamping surface 58 is opposed to the first clamping surface 56, and clamps a living body tissue in cooperation with the first clamping surface 56.

The moving mechanism 60 can move the first clamping surface 56 so as to apply tensile forces to the living body tissue, which is clamped between the first and second clamping surfaces 56 and 58, in directions perpendicular to the direction in which the first and second clamping bodies 52 and 54 can be relatively moved toward and away from each other by the pushing body 62. The pushing body 62 can apply a pressure to the living body tissue, can split, in cooperation with the moving mechanism 60, the living body tissue in the directions in which the above-described tensile forces are applied, and can apply tensile forces to the living body tissue so as to split the living body tissue.

In order to prevent the occurrence of a displacement of the first and second separate bodies 72 and 74 from each other in the opening/closing direction OC, it is preferable that a plurality of urging members 76 are disposed with a displacement in the opening/closing direction OC.

Although not illustrated, the first and second separate bodies 72 and 74 are directly connected to the distal end of the shaft 24. Thus, in this modification, the first clamping body 52 is not always necessary.

In connection with the first embodiment, the description has already been given of the operation at a time when the abutment portion 62a of the pushing body 62 pushes the oblique surfaces 72a and 74a of the first and second separate bodies 72 and 74 of the moving mechanism. Thus, this description is omitted here.

The first and second separate bodies 72 and 74 of the first modification can properly be substituted for first and second separate bodies 72 and 74 which will be described in a second modification illustrated in FIG. 6A.

A second modification of the first embodiment is described with reference to FIG. 6A to FIG. 6C.

Figure 6A:
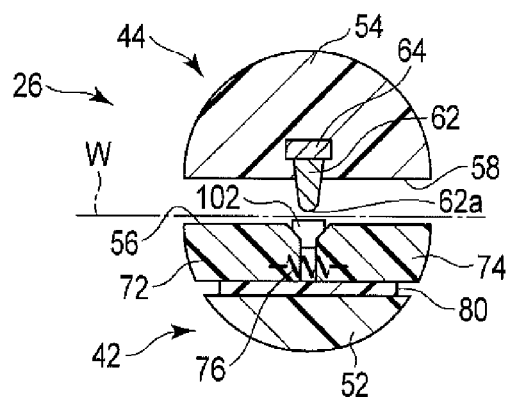
FIG. 6A is a schematic transverse cross-sectional view illustrating an end effector of a treatment instrument of a treatment system according to a second modification of the first embodiment, and illustrating a state in which first and second clamping surfaces are spaced apart, and an abutment portion of a pushing body is separated from a living body tissue.

As illustrated in FIG. 6A, a support portion 102, which supports the living body tissue and supports the abutment portion 62a of the pushing body 62, is disposed between the first and second separate bodies 72 and 74.

Figure 6B:
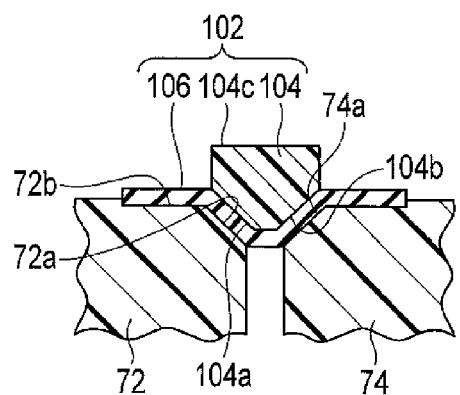
FIG. 6B is a schematic transverse cross-sectional view illustrating a support state of a support portion which is disposed on the oblique surfaces of the first and second separate bodies of the end effector of the treatment instrument of the treatment system according to the second modification of the first embodiment.

The support portion 102 illustrated in FIG. 6B includes a support body 104, and an extension/contraction body 106 functioning as an urging body which supports the support body 104. The extension/contraction body 106 is formed of an extensible/contractible material such as a rubber material. The extension/contraction body 106 is fixed to, for example, a fixing surface 72b of the first separate body 72, which is close to the first clamping surface 56 and oblique surface 72a, and is fixed to a fixing surface 74b of the second separate body 74, which is close to the first clamping surface 56 and oblique surface 74a. The extension/contraction body 106 urges the support body 104 in a direction away from the oblique surfaces 72a and 74a.

Here, the support body 104 is formed, for example, in a substantially trapezoidal shape, and includes inclined surfaces 104a and 104b which come in contact with the oblique surfaces 72a and 74a, and a support surface 104c which supports the abutment portion 62a of the pushing body 62. It is also preferable that the support body 104 has a triangular shape including the inclined surfaces 104a and 104b and support surface 104c.

Here, a living body tissue is placed on the first clamping surface 56 and the support surface 104c of the support body 104. In addition, when the support surface 104c is pushed by the abutment portion 62a of the pushing body 62 via the living body tissue, the support body 104 pushes, against the urging force of the extension/contraction body 106, the oblique surfaces 72a and 74a of the first and second separate bodies 72 and 74 by the inclined surfaces 104a and 104b. Thus, the first and second separate bodies 72 and 74 can be moved away from each other, and tensile forces are applied to the living body tissue in opposite directions, with the pushing body 62 being interposed.

In the meantime, if the pushing force of the abutment portion 62a of the pushing body 62 onto the support surface 104c is eliminated, the support body 104 can be moved by the function of the extension/contraction body 106, for example, to a position away from the oblique surfaces 72a and 74a. Thus, the first and second separate bodies 72 and 74 can be moved to approach each other.

Here, although the description has been given of the example in which the extension/contraction body 106, such as an extendible/contractible rubber material, is used as the urging body, it is also preferable that an elastic member, such as a plate spring, is used as the urging body in place of the extension/contraction body 106.

A support portion 102 illustrated in FIG. 6C includes a support body 104, and an urging body 108 which supports the support body 104. The urging body 108 is formed as a resisting body which resists the force that tries to compress the urging body 108. One end (lower end) of the urging body 108 is supported on a fixing surface 72c of the first separate body 72, and the other end (upper end) of the urging body 104 is fixed to a bottom surface of the support body 104. The urging body 108 urges the support body 104 so as to separate the support body 104 from the oblique surfaces 72a and 74a of the first and second separate bodies 72 and 74.

It is preferable that a coil spring, a rubber material or the like, for instance, which resists a compressing force, is used as the urging body 108.

Here, a living body tissue is placed on the first clamping surface 56 and the support surface 104c of the support body 104. In addition, when the support surface 104c is pushed by the abutment portion 62a of the pushing body 62 via the living body tissue, the support body 104 pushes, against the urging force by the urging body 108, the oblique surfaces 72a and 74a of the first and second separate bodies 72 and 74 by the inclined surfaces 104a and 104b. Thus, the first and second separate bodies 72 and 74 can be moved away from each other by the pushing body 62, and tensile forces are applied to the living body tissue in opposite directions, with the pushing body 62 being interposed.

In the meantime, if the pushing force of the abutment portion 62a of the pushing body 62 onto the support surface 104c is eliminated, the support body 104 can be moved by the function of the urging body 108, for example, to a position away from the oblique surfaces 72a and 74a. Thus, the first and second separate bodies 72 and 74 can be moved to approach each other.

The support body 104 of the second modification can properly be applied to the first and second separate bodies 72 and 74 which have been described in the first modification illustrated in FIG. 5.

A third modification of the first embodiment is described with reference to FIG. 7A and FIG. 7B.

As illustrated in FIG. 7A and FIG. 7B, a moving mechanism 120 includes first and second separate bodies 122 and 124, a link mechanism 126, and an urging member 128. The first and second separate bodies 122 and 124 are rotatably supported by a pivotal support shaft 130 at a position far from the first clamping surface 56. The link mechanism 126 includes a support body 132, a first link member 134 which is rotatably coupled to the support body 132, and a second link member 136 which is rotatably coupled to the support body 132. The first link member 134 is rotatably coupled to the first separate body 122, and the second link member 136 is rotatably coupled to the second separate body 124. In this modification, the urging member 128 urges the first and second separate bodies 122 and 124 to approach each other. In the meantime, as illustrated in FIG. 7A, when no pushing force is applied to the support body 132 by the abutment portion 62a of the pushing body 62, the support body 132 is clamped between the first and second separate bodies 122 and 124.

As illustrated in FIG. 7B, in this modification, the first clamping surface 56 of the first and second separate bodies 122 and 124 is not always formed as a planar surface, and a positional displacement occurs when the first and second separate bodies 122 and 124 move away from each other.

Here, a living body tissue is placed on the first clamping surface 56. In addition, when the support body 132 is pushed by the abutment portion 62a of the pushing body 62 via the living body tissue, the support body 132 approaches the pivotal support shaft 130 against the urging force by the urging member 128. Thus, the first and second separate bodies 122 and 124 can be rotated about the pivotal support shaft 130 of the first and second link members 134 and 136 by the pushing body 62, so that the first and second separate bodies 122 and 124 can be moved away from each other, and tensile forces are applied to the living body tissue in opposite directions, with the pressing body 62 being interposed.

In the meantime, if the pushing force of the abutment portion 62a of the pushing body 62 onto the support body 132 is eliminated, the support body 132 can be moved by the function of the urging member 128 to a position where the support body 132 is clamped between the first and second separate bodies 122 and 124. Thus, the first and second separate bodies 122 and 124 can be moved to approach each other.

A fourth modification of the first embodiment is described with reference to FIG. 8A and FIG. 8B. This modification is a modification of the third modification.

In the third modification, the description has been given of the example in which the urging member 128 is disposed between the first and second separate bodies 122 and 124. In the present modification, as illustrated in FIG. 8A and FIG. 8B, in place of the urging member 128, another urging member 128a is disposed between the support body 132 of the link mechanism 126 and the pivotal support shaft 130.

Also in this mode, as described in connection with the second modification, the first clamping surface 56 can be separated by the first and second separate bodies 122 and 124, and can be moved to restore to the state prior to the separation.

In the meantime, it is also preferable to use both the urging member 128 illustrated in FIG. 7A and FIG. 7B, and the urging member 128a illustrated in FIG. 8A and FIG. 8B.

A fifth modification of the first embodiment is described with reference to FIG. 9A and FIG. 9B. This modification is a modification of the third and fourth modifications.

Figure 9B:
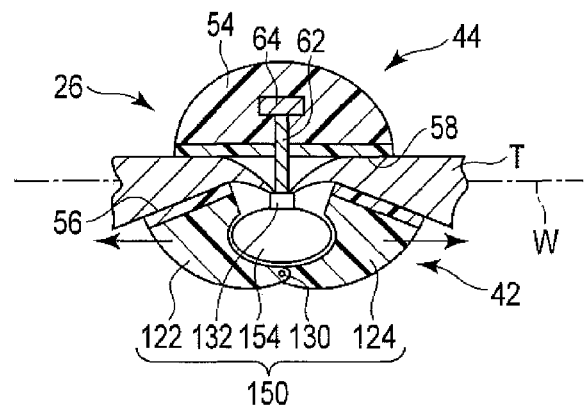
FIG. 9B is a schematic transverse cross-sectional view illustrating the end effector of the treatment instrument of the treatment system according to the fifth modification of the first embodiment, and illustrating a state in which the first and second clamping surfaces are moved to approach each other, a pushing force is applied to the living body tissue by the abutment portion of the pushing body, and first and second separate bodies are moved in directions away from each other.

As illustrated in FIG. 9A and FIG. 9B, a moving mechanism 150 includes first and second separate bodes 122 and 124, a support body 132, and an elastic deformation body 154. The first and second separate bodies 122 and 124 are rotatably supported by a pivotal support shaft 130 at a position far from the first clamping surface 56. Specifically, in this modification, the elastic deformation body 154 is disposed in place of the link mechanism 126.

The elastic deformation body 154 is coupled to the first and second separate bodies 122 and 124. The elastic deformation body 154 is formed, for example, in a cylindrical shape along the longitudinal direction L. If the elastic deformation body 154 is pushed radially inward by the support body 132 by the pushing force of the pushing body 62, the transverse cross section of the elastic deformation body 154 deforms gradually from a substantially circular shape into a flattened shape. Thus, the first and second separate bodies 122 and 124 can be moved away from each other by the pushing body 62, and tensile forces can be applied to the living body tissue in opposite directions, with the pressing body 62 being interposed.

In the meantime, if the pushing force of the abutment portion 62a of the pushing body 62 onto the support body 132 is eliminated, the elastic deformation body 154 is restored by elastic deformation from the flattened state to the original circular cylindrical state. Since the elastic deformation body 154 is coupled to the first and second separate bodies 122 and 124, the first and second separate bodies 122 and 124 can be moved to approach each other. In addition, the support body 132 can be moved to a position where the support body 132 is clamped between the first and second separate bodies 122 and 124.

Next, a second embodiment is described with reference to FIG. 10A and FIG. 10B. This embodiment is a modification of the first embodiment including the respective modifications. The same members as described in the first embodiment, or the members having the same functions as in the first embodiment, are denoted by like reference numerals as much as possible, and a detailed description thereof is omitted.

Figure 10A:
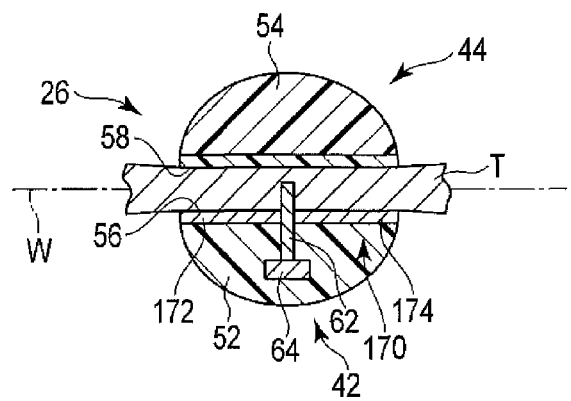
FIG. 10A is a schematic transverse cross-sectional view illustrating an end effector of a treatment instrument of a treatment system according to a second embodiment, and illustrating a state in which a living body tissue is clamped between first and second clamping surfaces, while a pushing force is being applied to the living body tissue by an abutment portion of a pushing body.
Figure 10B:
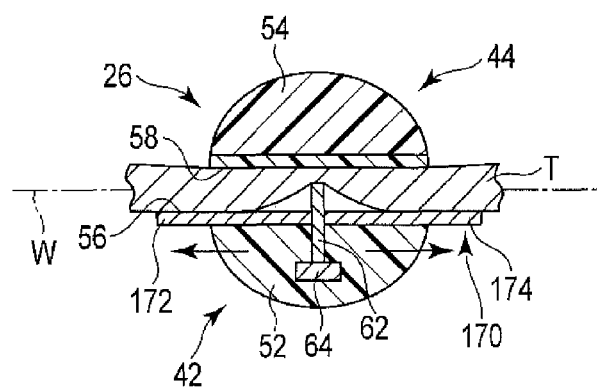
FIG. 10B is a schematic transverse cross-sectional view illustrating the end effector of the treatment instrument of the treatment system according to the second embodiment, and illustrating a state in which thermal deformation members disposed on the first clamping surface are heated and deformed and first and second separate bodies are moved in directions away from each other, in the state in which the living body tissue is clamped between the first and second clamping surfaces while the pushing force is being applied to the living body tissue by the abutment portion of the pushing body.

As illustrated in FIG. 10A and FIG. 10B, a first clamping portion 42 according to this embodiment includes a first clamping body 52, a first clamping surface 56, a moving mechanism 170, and a pushing body 62. Specifically, unlike the first embodiment, the pushing body 62 is disposed in the first clamping portion 42, and the pushing body 62 is removed from the second clamping portion 44.

The moving mechanism 170 according to this embodiment includes first and second separate bodies 172 and 174 which deform if heat is applied, and move toward mutually opposite sides along the width direction W. In this embodiment, the first and second separate bodies 172 and 174 are thermal deformation members which deform when heat is applied. As the thermal deformation members, use is made of a shape memory alloy such as a nickel-titanium alloy, or use is made of a bimetal which deforms with different coefficients of thermal expansion. Although not illustrated, it is preferable that the thermal deformation members are heated by a heater which is, for example, the same as the heater 64 that heats the pushing body 62.

Next, the operation of the treatment system 10 according to this embodiment is described in brief.

The opening/closing knob 32 is operated to clamp a living body tissue between the first and second clamping surfaces 56 and 58. At this time, the living body tissue is pushed by the abutment portion 62a of the pushing body 62.

In this state, the first and second separate bodies 172 and 174 are heated. As illustrated in FIG. 10B, the first and second separate bodies 172 and 174 deform in a manner to apply tensile forces to the living body tissue in mutually opposite directions, with the pushing body 62 being interposed. Specifically, the living body tissue is moved in directions perpendicular to the direction of movement of the pushing body 62. Thus, tensile forces are applied to the living body tissue in directions perpendicular to the direction of pushing by the pushing body 62. In other words, such forces as to split the living body tissue are applied toward mutually opposite sides, with the abutment portion 62a of the pushing body 62 being interposed.

Here, for example, when the living body tissue has become fragile or thin, the living body tissue can be split without supplying energy to the heater 64 from the energy source 14, or after finishing the application of the energy. Needless to say, it is also preferable that the living body tissue is split while heating the living body tissue by the abutment portion 62a of the pushing body 62 by supplying energy to the heater 64 from the energy source 14.

Besides, for example, when the living body tissue is relatively thick, the pushing body 62 is heated by supplying energy to the heater 64 from the energy source 14. At this time, the abutment portion 62a of the pushing body 62 is heated up to, for example, about 200° C. to 350° C. In addition, tensile forces toward mutually opposite sides are applied to that part of the living body tissue, which is put in contact with the abutment portion 62a of the pushing body 62, while hemostasis of this part is being effected by heat. In this manner, since the tensile forces toward the mutually opposite sides are applied to the symmetric positions with the pushing body 62 being interposed, the living body tissue can be split.

As has been described above, according to the treatment system 10 of the present embodiment, the following can be said.

The first and second separate bodies 172 and 174 of the moving mechanism 170 can separate the first clamping surface 56 such that the first clamping surface 56 is movable in directions perpendicular to the direction of movement (opening/closing direction OC) of the pushing body 62 and in mutually opposite directions. Thus, in the state in which the living body tissue, which is pushed by the abutment portion 62a of the plate-shaped pushing body 62, is pushed on the first and second separate bodies 172 and 174, the first and second separate bodies 172 and 174 can be heated and deformed, and the first and second separate bodies 172 and 174 can be moved toward mutually opposite sides, with the abutment portion 62a being interposed. Thus, the tensile forces toward opposite sides, with the pushing body 62 being interposed, can be applied to the living body tissue which is pushed by the abutment portion 62a of the pushing body 62. Accordingly, even if the abutment portion 62a is not sharp, the living body tissue can easily be split.

In this manner, according to the treatment instrument 12 of this embodiment, in the state in which the living body tissue is clamped, the clamped living body tissue can easily be split.

Figure 11A:
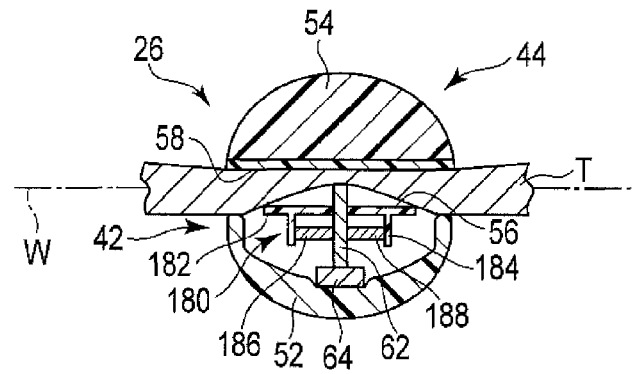
FIG. 11A is a schematic transverse cross-sectional view illustrating an end effector of a treatment instrument of a treatment system according to a first modification of the second embodiment, and illustrating a state in which a living body tissue is clamped between first and second clamping surfaces, while a pushing force is being applied to the living body tissue by an abutment portion of a pushing body.
Figure 11B:
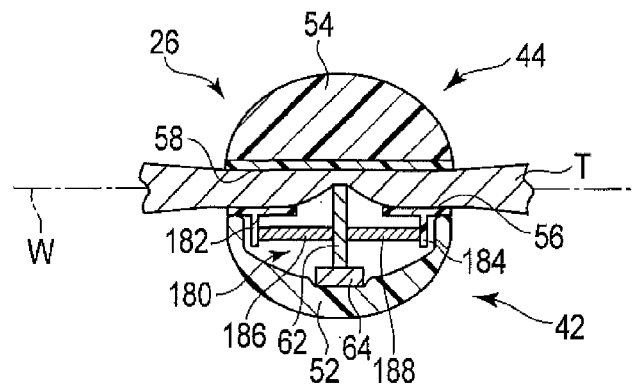
FIG. 11B is a schematic transverse cross-sectional view illustrating the end effector of the treatment instrument of the treatment system according to the first modification of the second embodiment, and illustrating a state in which thermal deformation members disposed on the first clamping surface are heated and deformed and first and second separate bodies are moved in directions away from each other, in the state in which the living body tissue is clamped between the first and second clamping surfaces while the pushing force is being applied to the living body tissue by the abutment portion of the pushing body.

A first modification of the second embodiment is described with reference to FIG. 11A and FIG. 11B.

A moving mechanism 180 included in a first clamping portion 42 according to this modification includes first and second separate bodies 182 and 184, and first and second thermal deformation members 186 and 188 which are coupled to the pushing body 62 and deformed by heat conveyed from the pushing body 62. As the first and second thermal deformation members 186 and 188, use is made of a shape memory alloy such as a nickel-titanium alloy, or use is made of a bimetal which deforms with different coefficients of thermal expansion.

Each of the first and second separate bodies 182 and 184 of the moving mechanism 180 according to this modification has a cross section formed in a substantially T shape. The first and second separate bodies 182 and 184 can be moved in mutually opposite directions along the width direction W by the slide mechanism 80 described in the first embodiment.

Next, the operation of the treatment system 10 according to this modification is described in brief.

The opening/closing knob 32 is operated to clamp a living body tissue between the first and second clamping surfaces 56 and 58. At this time, the living body tissue is pushed by the abutment portion 62a of the pushing body 62.

In this state, if the pushing body 62 is heated by the heater 64, the heat is conveyed to the first and second thermal deformation members 186 and 188, and the first and second thermal deformation members 186 and 188 are heated and deformed. As illustrated in FIG. 11B, in accordance with the deformation of the first and second thermal deformation members 186 and 188, the first and second separate bodies 182 and 184 move in a manner to apply tensile forces to the living body tissue in opposite directions, with the pushing body 62 being interposed. Specifically, the living body tissue is moved in directions perpendicular to the direction of movement of the pushing body 62. Thus, tensile forces are applied to the living body tissue in directions perpendicular to the direction of pushing by the pushing body 62. In other words, such forces as to split the living body tissue are applied toward the mutually opposite sides, with the abutment portion 62a of the pushing body 62 being interposed.

As has been described above, according to the treatment system 10 of the present embodiment, the following can be said.

The first and second separate bodies 182 and 184 of the moving mechanism 180 can separate the first clamping surface 56 such that the first clamping surface 56 is movable in directions perpendicular to the direction of movement (opening/closing direction OC) of the pushing body 62 and in mutually opposite directions. Thus, in the state in which the living body tissue, which is pushed by the abutment portion 62a of the plate-shaped pushing body 62, is pushed on the first and second separate bodies 182 and 184, the first and second thermal deformation members 186 and 188 can be heated and deformed, and the first and second separate bodies 182 and 184, which are coupled to the first and second thermal deformation members 186 and 188, can be moved toward mutually opposite sides, with the abutment portion 62a being interposed. Thus, the tensile forces toward opposite sides, with the pushing body 62 being interposed, can be applied to the living body tissue which is pushed by the abutment portion 62a of the pushing body 62. Accordingly, even if the abutment portion 62a is not sharp, the living body tissue can easily be split.

In this manner, according to the treatment instrument 12 of this modification, in the state in which the living body tissue is clamped, the clamped living body tissue can easily be split.

A second modification of the second embodiment is described with reference to FIG. 12A and FIG. 12B.

Figure 12A:
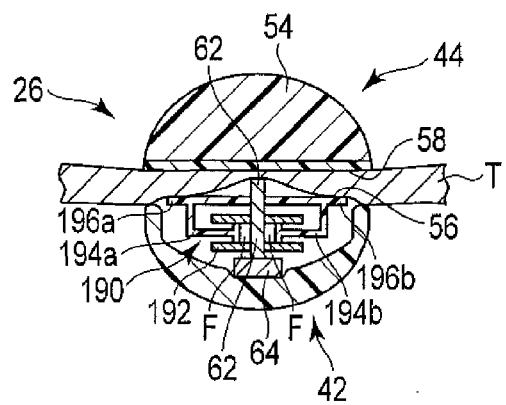
FIG. 12A is a schematic transverse cross-sectional view illustrating an end effector of a treatment instrument of a treatment system according to a second modification of the second embodiment, and illustrating a state in which a living body tissue is clamped between first and second clamping surfaces, while a pushing force is being applied to the living body tissue by an abutment portion of a pushing body.

As illustrated in FIG. 12A and FIG. 12B, a moving mechanism 190 includes a cylinder 192 in which a fluid such as a liquid with biocompatibility, preferably physiological saline, is contained; pistons (steam-pressure driving portions) 194a and 194b which are disposed in the cylinder 192; and moving bodies (steam-pressure driving portions) 196a and 196b which are coupled to the pistons 194a and 194b and move in accordance with the movement of the pistons 194a and 194b. The volume of the fluid F, which is contained in the cylinder 192, can easily be adjusted, for example, when temperatures are varied. The moving bodies 196a and 196b cooperate to form the first clamping surface 56. The cylinder 192, together with the pushing body 62, is heated by the heater 64. The pistons 194a and 194b, which are disposed in the cylinder 192, can move in mutually opposite directions along with the width direction W, with the pushing body 62 being interposed.

If the pushing body 62 is heated by the heater 64, the fluid F of liquid in the cylinder 192 is vaporized by the heat. Since the volume in the cylinder 192 increases, the pistons 194a and 194b move along the width direction W in directions away from each other, and the moving bodies 196a and 196b, which are coupled to the pistons 194a and 194b, move along the width direction W in directions away from each other.

In this manner, if the fluid F of liquid is heated and vaporized and the volume is increased to move the pistons 194a and 194b away from each other, tensile forces can be applied to the living body tissue by the moving bodies 196a and 196b. Accordingly, even if the abutment portion 62a is not sharp, the living body tissue can easily be split.

In the meantime, if the supply of heat to the pushing body 62 from the heater 64 is stopped, the vaporized fluid F is cooled and liquefied, and the volume in the cylinder 192 decreases to move the pistons 194a and 194b to approach each other.

A third modification of the second embodiment is described with reference to FIG. 13A and FIG. 13B.

As illustrated in FIG. 13A and FIG. 13E, a moving mechanism 200 includes a cylinder 202; pistons 204a and 204b which are disposed in the cylinder 202; and moving bodies (separate bodies) 206a and 206b which are coupled to the pistons 204a and 204b and move in accordance with the movement of the pistons 204a and 204b. The moving bodies 206a and 206b cooperate to form the first clamping surface 56. The pistons 204a and 204b, which are disposed in the cylinder 202, can move in mutually opposite directions along with the width direction W, with the pushing body 62 being interposed.

In this modification, unlike the second modification of the second embodiment, there is no need to put a liquid in the cylinder 202 in advance. If the pushing body 62 is heated by the heater 64, the heat is conveyed to the living body tissue from the abutment portion 62a of the pushing body 62. By the heat, steam S occurs from the living body tissue. Thus, the steam S is filled in the cylinder 202, and the pistons 204a and 204b move along the width direction W in directions away from each other. In addition, the moving bodies 206a and 206b, which are coupled to the pistons 204a and 204b, move along the width direction W in directions away from each other.

In this manner, the living body tissue is heated by the heat from the heater 64, and steam is produced. In accordance with this, tensile forces can be applied to the living body tissue, which is pushed by the abutment portion 62a of the pushing body 62, toward opposite sides with the pushing body 62 being interposed. Accordingly, even if the abutment portion 62a is not sharp, the living body tissue can easily be split.

In the meantime, if the supply of heat to the pushing body 62 from the heater 64 is stopped, the steam S no longer occurs from the living body tissue, and the steam already produced from the living body tissue is cooled and liquefied. The volume in the cylinder 202 decreases, and the pistons 204a and 204b are moved to approach each other.

Next, a third embodiment is described with reference to FIG. 14. This embodiment is a modification of the first and second embodiments including the respective modifications. The same members as described in the first and second embodiments, or the members having the same functions as in the first and second embodiments, are denoted by like reference numerals as much as possible, and a detailed description thereof is omitted.

Figure 14:
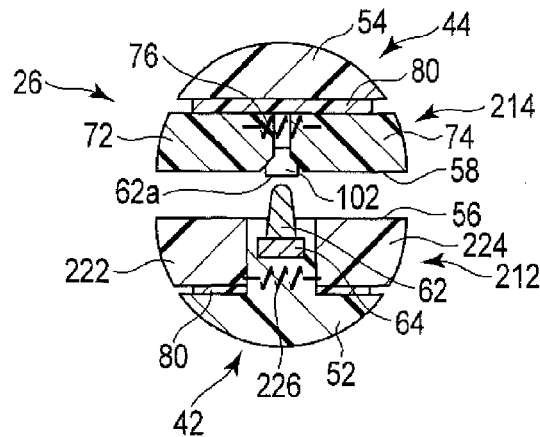
FIG. 14 is a schematic transverse cross-sectional view illustrating a state in which moving mechanisms are disposed, respectively, on first and second clamping surfaces of an end effector of a treatment instrument of a treatment system according to a third embodiment, and the first and second clamping surfaces are spaced apart.

As illustrated in FIG. 14, a first moving mechanism 212 and a pushing body 62 are disposed in the first clamping portion 42, and a second moving mechanism 214 is disposed in the second clamping portion 44. Specifically, the first clamping portion 42 includes a first clamping body 52, a first clamping surface 56, the first moving mechanism 212 provided on the first clamping surface 56, and the pushing body 62. The second clamping portion 44 includes a second clamping body 54, a second clamping surface 58, and the second moving mechanism 214 provided on the second clamping surface 58.

The first moving mechanism 212 is formed like the moving mechanism 60 described in the first embodiment. Here, for the purpose of convenience in the description, the description is given by adding reference numeral 222 to the first separate body of the first moving mechanism 212, adding reference numeral 224 to the second separate body, and adding reference numeral 226 to the urging member, such as a coil spring, which resists tensile forces. The first and second separate bodies 222 and 224 are movable by the slide mechanism 80. In the meantime, in this embodiment, the pushing body 62 is fixed to the first clamping body 52.

The second clamping portion 44 of this embodiment has the same configuration as the first clamping portion 42 of the second modification of the first embodiment illustrated in FIG. 6A, so a description thereof is omitted.

Next, the operation of the treatment system 10 according to this embodiment is described.

The opening/closing knob 32 is operated to clamp a living body tissue between the first and second clamping surfaces 56 and 58. At this time, the living body tissue is pushed by the abutment portion 62a of the pushing body 62, and the support body 104 of the support portion 102 is pushed. Thus, the first and second separate bodies 72 and 74 of the second clamping portion 44 are moved away from each other, and tensile forces are applied to the living body tissue in opposite directions, with the pushing body 62 being interposed.

In this manner, with the tensile forces being applied to the living body tissue, the first and second separate bodies 222 and 224 of the first clamping portion 42 move away from each other in an interlocking fashion, and tensile forces are applied to the living body tissue in opposite directions, with the pushing body 62 being interposed.

Accordingly, even if the abutment portion 62a is not sharp, the living body tissue is easily split.

In the meantime, if the pushing force of the abutment portion 62a of the pushing body 62 of the first clamping portion 42 onto the support body 104 of the second clamping portion 44 is eliminated, the support body 104 of the second clamping portion 44 can be separated to a position away from the oblique surfaces 72a and 74a of the first and second separate bodies 72 and 74 of the second clamping portion 44. Thus, the first and second separate bodies 72 and 74 of the second clamping portion 44 can be moved to approach each other.

On the other hand, in the first clamping portion 42, the first and second separate bodies 222 and 224 are moved to approach each other by the urging member 226, in accordance with the mutual approaching between the first and second separate bodies 72 and 74 of the second clamping portion 44.

In this manner, according to the treatment instrument 12 of this embodiment, in the state in which the living body tissue is clamped, the clamped living body tissue can easily be split.

For example, in the case of a living body tissue with a relatively large thickness, heat is applied to the living body tissue from the abutment portion 62a of the pushing body 62. Thereby, even if the abutment portion 62a is not sharp, the living body tissue is easily split.

Therefore, according to the treatment system 10 of this embodiment, in the state in which the living body tissue is clamped, the clamped living body tissue can easily be split.

In the first embodiment, as illustrated in FIG. 3A and FIG. 3B, the example was described in which the moving mechanism 60 is disposed on the first clamping surface 56, and the pushing body 62 is disposed on the second clamping surface 58. In the second embodiment, as illustrated in FIG. 10A and FIG. 10B, the example was described in which the moving mechanism 170 and pushing body 62 are disposed on the first clamping surface 56. In the present embodiment, the moving mechanisms are disposed on the first and second clamping surfaces 56 and 58, respectively.

In this case, the living body tissue between the first and second clamping surfaces 56 and 58 can be moved in mutually opposite directions along the width direction W. Thus, tensile forces, which facilitate splitting of the living body tissue, can be applied to both the first clamping surface 56 side and the second clamping surface 58 side of the living body tissue.

A first modification of the third embodiment is described with reference to FIG. 15.

Figure 15:
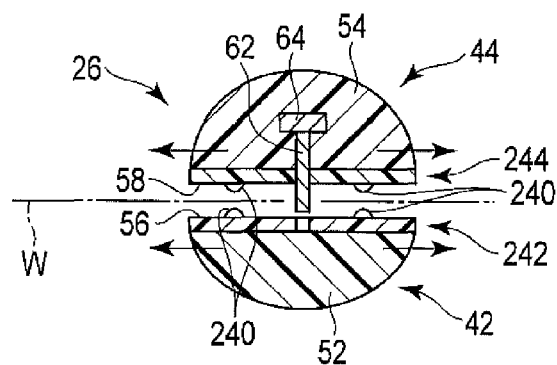
FIG. 15 is a schematic transverse cross-sectional view illustrating an end effector of a treatment instrument of a treatment system according to a first modification of the third embodiment, and illustrating a state in which first and second clamping surfaces are spaced apart, an abutment portion of an pushing body provided on the second clamping surface is separated from a living body tissue, and separate bodies provided on the first and second clamping surfaces, respectively, are kept in close proximity.

As illustrated in FIG. 15, in this modification, the first clamping portion 42 includes a first clamping body 52, a first clamping surface 56, and a first moving mechanism 242. The second clamping portion 44 includes a second clamping body 54, a second clamping surface 58, a second moving mechanism 244, and a pushing body 62. As described in the first modification of the first modification, the first and second clamping bodies 52 and 54 may be absent.

As the first and second moving mechanisms 242 and 244, the moving mechanisms described in the first and second embodiments including the respective modifications may be used where necessary. Thus, by pressing the living body tissue by the abutment portion 62a of the pushing body 62, tensile forces toward mutually opposite sides can be applied to the living body tissue at the symmetrical positions with the pushing body 62 being interposed.

Projections 240 for preventing a slip of the living body tissue are formed on the first and second clamping surfaces 56 and 58. When the living body tissue is clamped between the first and second clamping surfaces 56 and 58, the projections 240 can prevent the clamped living body tissue from slipping and escaping from the first and second clamping surfaces 56 and 58.

In FIG. 15, although the projections 240 are disposed on both the first and second clamping surfaces 56 and 58, the projections 240 may be formed on only one of the first and second clamping surfaces 56 and 58. Although FIG. 15 depicts only two projections 240 formed along the width direction W, the number and size of projections 240 may properly be set.

In the meantime, for example, when the moving mechanism 60 described in the first embodiment or the moving mechanism 170 described in the second embodiment is used, it is preferable that the projections 240 are formed on the first clamping surface 56 which moves when tensile force is applied to the living body tissue.

The portions, which prevent a slip of the living body tissue clamped between the first and second clamping surfaces 56 and 58, are not limited to the projections 240, and it is preferable that the first and second clamping surfaces 56 and 58 themselves are formed as rough surfaces such as satin-finished surfaces.

A second modification of the third embodiment is described with reference to FIG. 16.

Figure 16:
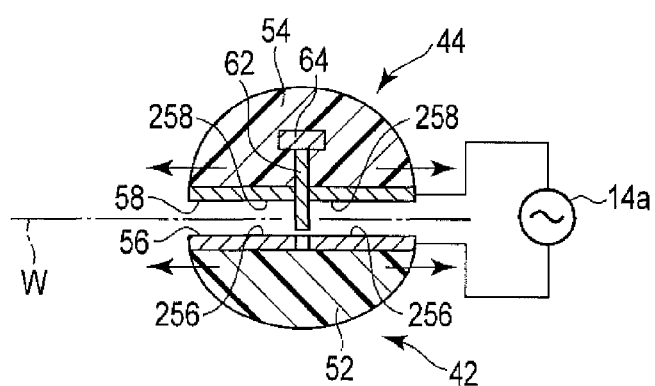
FIG. 16 is a schematic transverse cross-sectional view illustrating an end effector of a treatment instrument of a treatment system according to a second modification of the third embodiment, and illustrating a state in which first and second clamping surfaces are spaced apart, and an abutment portion of a pushing body is separated from a living body tissue.

As illustrated in FIG. 16, energy output portions 256 and 258, which can output energy, aside from the supply of energy to the heater 64, are disposed on the first and second clamping surfaces 56 and 58. The energy output portions 256 and 258 are connected to an energy source (controller) 14. The outputs of the energy output portions 256 and 258 are operated by, for example, a footswitch. In the meantime, in this modification, high-frequency electrodes are used for the energy output portions 256 and 258.

A high-frequency current is caused to flow, from the energy source 14, between the energy output portions 256 and 258 in the state in which the living body tissue is clamped therebetween. Thereby, by Joule heat, sealing (hemostasis) of the living body tissue can be effected along with the splitting of the living body tissue by the pushing body 62.

In the meantime, it is preferable to treat the living body tissue that is clamped between the first and second clamping surfaces 56 and 58, by causing a high-frequency current to flow, from the energy source 14, between the energy output portions 256 and 258 in the state in which the living body tissue is clamped therebetween, while the pushing body 62 is being heated by the heater 64.

Depending on the thickness of the living body tissue, it is not always necessary to heat the pushing body 62. However, since it is necessary to effect hemostasis (sealing) of the split living body tissue, it becomes necessary to heat the pushing body 62, or to coagulate the living body tissue by some other proper means. As other proper means for coagulating the living body tissue, use may be made of, for example, high-frequency energy or ultrasonic vibration energy. Specifically, instead of using the high-frequency electrodes, the energy output portions 256 and 258 may use a heater similar to the heater 64 described in the first embodiment, or may use an ultrasonic transducer (not shown) or the like which coagulates the living body tissue by ultrasonic vibrations.

In addition, in this modification, although the energy output portions 256 are disposed on the first clamping surface 56 and the energy output portions 258 are disposed on the second clamping surface 58, it is also preferable that the energy output portions are disposed on only one of the first and second clamping surfaces 56 and 58.

Figure 17:
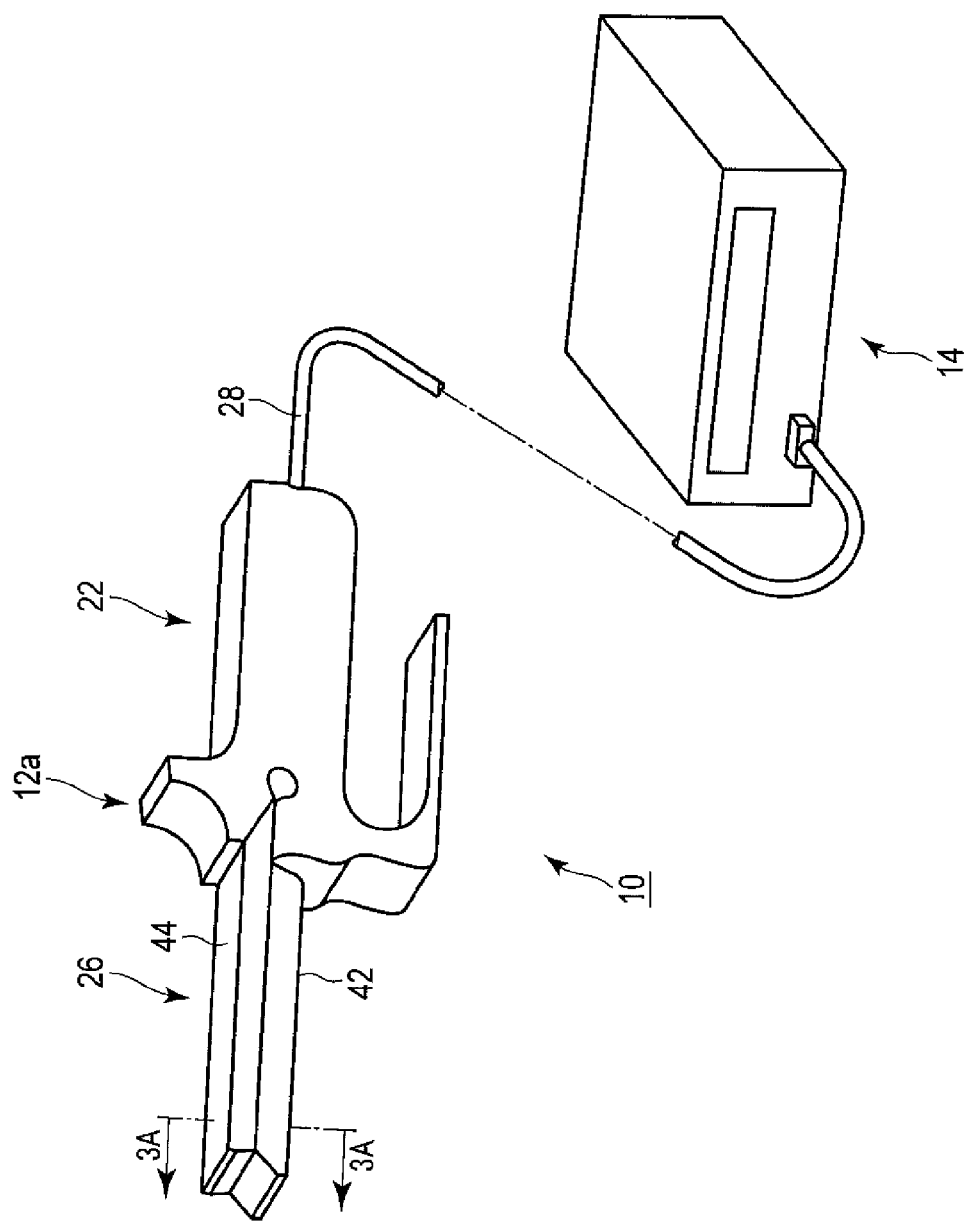
FIG. 17 is a schematic perspective view illustrating a modification of the treatment instrument of the treatment system according to the first to third embodiments including the respective modifications.

In the meantime, in the above-described first to third embodiments, the example was described in which the shaft 24 is disposed between the end effector 26 and the handle 22. However, as illustrated in FIG. 17, it is also preferable that the end effector 26 is directly connected to the handle 22. In short, the shaft 24 is not always necessary.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment instrument comprising:
   a first clamping surface which is formed by a first separate body and a second separate body;
   a second clamping surface which is opposed to the first clamping surface such that the second clamping surface is capable of relatively approaching, and moving away from, the first clamping surface, and which is configured to clamp a living body tissue with the first clamping surface by causing the first clamping surface to relatively approach the second clamping surface;
   a pressure application member which is provided on the second clamping surface, and which includes an abutment portion extending in a line shape and configured to apply a pressure to the living body tissue in a line shape by causing the first and second clamping surfaces to relatively approach each other; and
   a moving mechanism which includes a support body provided between the first separate body and the second separate body such that the support body is configured to directly contact the abutment portion when the first clamping surface and the second clamping surface are closed without tissue therebetween, and which is configured to move the first clamping surface in a manner to apply tensile forces to the living body tissue clamped between the first clamping surface and the second clamping surface, in directions deviating away from a direction along a line formed on the living body tissue by the pressure application member.

2. The treatment instrument of claim 1, wherein the first separate body and the second separate body are configured to be movable in directions perpendicular to a direction of movement of the pressure application member, which is provided on the second clamping surface, and in mutually opposite directions, and to separate the first clamping surface.

3. The treatment instrument of claim 2, wherein the first separate body and the second separate body are urged to approach or abut on each other.

4. The treatment instrument of claim 2, wherein the support body is configured to support the pressure application member in accordance with splitting of the living body tissue, and to relatively move, when a pressure is applied by the pressure application member via the living body tissue, the first separate body and the second separate body to opposite sides such that the first and second separate bodies move away from each other.

5. The treatment instrument of claim 4, wherein the moving mechanism includes an urging body configured to support the support body and to move the first separate body and the second separate body such that the first separate body and the second separate body move away from each other when a pressure is applied to the support body by the pressure application member, wherein the first separate body and the second separate body approach each other when the pressure application member is separated from the support body.

6. The treatment instrument of claim 1, wherein the abutment portion of the pressure application member is configured to apply the pressure to the living body tissue in the line shape, and capable of applying thermal energy to the living body tissue.

7. The treatment instrument of claim 1, wherein the abutment portion of the pressure application member is configured to abut the living body tissue, the abutment portion including a part with a blunt shape which applies the pressure to the living body tissue in the line shape.

8. The treatment instrument of claim 1, wherein at least one of the first clamping surface and the second clamping surface includes a projection configured to prevent a slip of the living body tissue.

9. The treatment instrument of claim 1, wherein at least one of the first clamping surface and the second clamping surface includes an energy output portion configured to output energy for sealing the living body tissue.

10. The treatment instrument of claim 1, further comprising a heater configured to convey heat to the pressure application member.

11. The treatment instrument of claim 10, further comprising:
a first clamping body including the first clamping surface; and
a second clamping body including the second clamping surface,
wherein the heater is provided between the pressure application member and the second clamping body.

12. The treatment instrument of claim 1, wherein the support body comprises:
a support surface configured to engage with the abutment portion;
a first inclined surface located on one side of the support surface and configured to contact with the first separate body; and
a second inclined surface located on an opposite side of the support surface and configured to contact the second separate body.

13. The treatment instrument of claim 12, wherein when the support surface is pushed by the abutment portion via the living body tissue, the support body is configured to push the first inclined surface and the second inclined surface against the first separate body and the second separate body such that the first separate body and the second separate body move apart from each other.

* * * * *